(12) United States Patent
Galen et al.

(10) Patent No.: US 9,415,235 B2
(45) Date of Patent: Aug. 16, 2016

(54) VAGINAL REMODELING DEVICE AND METHOD

(71) Applicant: VIVEVE, INC., Sunnyvale, CA (US)

(72) Inventors: Donald I. Galen, Sunnyvale, CA (US); Jerome Jackson, Sunnyvale, CA (US); Steven Marc Lopez, Sunnyvale, CA (US); Russell Meirose, Sunnyvale, CA (US); Ian F. Smith, Sunnyvale, CA (US); Srihari Yamanoor, Sunnyvale, CA (US)

(*) Notice: Subject to any disclaimer, the term of this patent is extended or adjusted under 35 U.S.C. 154(b) by 655 days.

(21) Appl. No.: 13/835,748

(22) Filed: Mar. 15, 2013

(65) Prior Publication Data
US 2013/0245728 A1  Sep. 19, 2013

(30) Foreign Application Priority Data

Mar. 16, 2012  (CN) .......................... 2012 1 0069906

(51) Int. Cl.
*A61F 7/12*    (2006.01)
*A61N 5/00*    (2006.01)
(Continued)

(52) U.S. Cl.
CPC .............. *A61N 5/00* (2013.01); *A61B 18/1485* (2013.01); *A61B 2018/00023* (2013.01);
(Continued)

(58) Field of Classification Search
CPC ................. A61B 18/1485; A61B 2018/00023; A61B 2018/00821; A61B 2018/1861; A61B 2018/00559; A61B 19/5244; A61N 2005/005; A61N 2005/007; A61N 2007/0043
See application file for complete search history.

(56) References Cited

U.S. PATENT DOCUMENTS 2,811,969 A * 11/1957 Shubert .............. A61B 17/4208
                                                       401/8
3,595,217 A *  7/1971 Rheinfrank ........ A61B 10/0241
                                                       600/566
(Continued)

FOREIGN PATENT DOCUMENTS

CN        1778414        5/2006
CN        2897183 Y      5/2007
(Continued)

OTHER PUBLICATIONS

Chinese Office Action, Nov. 25, 2014, for Chinese App'l No. 201080049557.4, filed May 18, 2012.
(Continued)

*Primary Examiner* — Kaitlyn Smith
(74) *Attorney, Agent, or Firm* — Law Offices of Albert Wai-kit Chan, PLLC

(57) ABSTRACT

This invention provides devices and methods for remodeling the female genital tissue, the device comprising a treatment tip, wherein the distal end of the treatment tip is conical, spherical, hemispherical, oval or circular in shape. The device further comprises one or more energy delivery elements for simultaneous cooling of the vaginal epithelium and transmission of energy for heating the tissues underneath the epithelium. In one embodiment, said device may further comprise one or more of the following: one or more temperature sensors for measuring the temperature at or below the epithelium; one or more directional sensors mounted on the hand piece or treatment tip; and one or more depth markers to show the depth of penetration of the treatment tip into the vagina. In another embodiment, this invention provides a device having a finger holder with electrodes for remodeling the female genital tissue.

20 Claims, 12 Drawing Sheets

(51) Int. Cl.
*A61B 18/14* (2006.01)
*A61B 18/00* (2006.01)
*A61B 18/18* (2006.01)
*A61N 7/00* (2006.01)

(52) U.S. Cl.
CPC ........... *A61B 2018/00559* (2013.01); *A61B 2018/00791* (2013.01); *A61B 2018/147* (2013.01); *A61B 2018/1495* (2013.01); *A61B 2018/1838* (2013.01); *A61B 2018/1853* (2013.01); *A61B 2018/1861* (2013.01); *A61N 7/00* (2013.01)

(56) References Cited

U.S. PATENT DOCUMENTS

| | | | |
|---|---|---|---|
| 3,741,211 A * | 6/1973 | Vreeland, Jr. | A61B 10/0241 604/272 |
| 3,995,629 A * | 12/1976 | Patel | A61B 17/42 604/117 |
| 4,326,529 A | 4/1982 | Doss et al. | |
| 4,381,007 A | 4/1983 | Doss et al. | |
| 4,785,807 A | 11/1988 | Blanch | |
| 4,785,828 A | 11/1988 | Maurer | |
| 4,892,520 A * | 1/1990 | Gilbaugh | A61B 10/0241 604/117 |
| 4,907,589 A | 3/1990 | Cosman | |
| 4,920,978 A | 5/1990 | Colvin | |
| 4,976,709 A | 12/1990 | Sand | |
| 4,989,614 A * | 2/1991 | Dejter, Jr. | A61B 10/0283 600/565 |
| 5,046,511 A | 9/1991 | Maurer et al. | |
| 5,143,063 A | 9/1992 | Fellner | |
| 5,160,334 A | 11/1992 | Billings et al. | |
| 5,230,349 A | 7/1993 | Langberg | |
| 5,242,440 A * | 9/1993 | Shippert | A61B 17/00 200/DIG. 2 |
| 5,301,692 A | 4/1994 | Knowlton | |
| 5,330,469 A | 7/1994 | Fleenor | |
| 5,334,193 A | 8/1994 | Nardella | |
| 5,348,554 A | 9/1994 | Imran et al. | |
| 5,409,453 A * | 4/1995 | Lundquist | A61B 10/0233 604/22 |
| 5,449,374 A | 9/1995 | Dunn et al. | |
| 5,458,596 A | 10/1995 | Lax et al. | |
| 5,469,857 A | 11/1995 | Laurent et al. | |
| 5,569,242 A | 10/1996 | Lax et al. | |
| 5,660,836 A | 8/1997 | Knowlton | |
| 5,755,753 A | 5/1998 | Knowlton | |
| 5,765,567 A | 6/1998 | Knowlton | |
| 5,824,076 A | 10/1998 | Knowlton | |
| 5,871,524 A | 2/1999 | Knowlton | |
| 5,919,219 A | 7/1999 | Knowlton | |
| 5,937,863 A | 8/1999 | Knowlton | |
| 5,947,891 A | 9/1999 | Morrison | |
| 5,948,011 A | 9/1999 | Knowlton | |
| 5,951,550 A | 9/1999 | Shirley et al. | |
| 5,954,717 A | 9/1999 | Behl et al. | |
| 5,986,446 A * | 11/1999 | Williamson | G01R 1/06788 324/149 |
| 6,002,968 A | 12/1999 | Edwards | |
| 6,024,743 A | 2/2000 | Edwards | |
| 6,035,238 A * | 3/2000 | Ingle | A61B 18/1485 607/101 |
| 6,044,847 A | 4/2000 | Carter et al. | |
| 6,081,749 A * | 6/2000 | Ingle | A61B 18/1485 606/41 |
| 6,091,995 A | 7/2000 | Ingle et al. | |
| 6,139,569 A | 10/2000 | Ingle et al. | |
| 6,156,060 A | 12/2000 | Roy et al. | |
| 6,216,704 B1 | 4/2001 | Ingle et al. | |
| 6,236,891 B1 | 5/2001 | Ingle et al. | |
| 6,241,753 B1 | 6/2001 | Knowlton | |
| 6,277,116 B1 | 8/2001 | Utely et al. | |
| 6,283,987 B1 | 9/2001 | Laird et al. | |
| 6,292,700 B1 | 9/2001 | Morrison | |
| 6,311,090 B1 | 10/2001 | Knowlton | |
| 6,322,584 B2 | 11/2001 | Ingle et al. | |
| 6,350,276 B1 | 2/2002 | Knowlton | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 | 7/2002 | Stern | |
| 6,416,504 B2 | 7/2002 | Mosel et al. | |
| 6,425,912 B1 | 7/2002 | Knowlton | |
| 6,427,089 B1 | 7/2002 | Knowlton | |
| 6,430,446 B1 | 8/2002 | Knowlton | |
| 6,438,424 B1 | 8/2002 | Knowlton | |
| 6,453,202 B1 | 9/2002 | Knowlton | |
| 6,461,332 B1 | 10/2002 | Mosel et al. | |
| 6,461,378 B1 | 10/2002 | Knowlton | |
| 6,470,216 B1 | 10/2002 | Knowlton | |
| 6,478,791 B1 | 11/2002 | Carter et al. | |
| 6,480,746 B1 | 11/2002 | Ingle et al. | |
| 6,482,204 B1 | 11/2002 | Lax et al. | |
| 6,533,780 B1 | 3/2003 | Laird et al. | |
| 6,546,934 B1 | 4/2003 | Ingle et al. | |
| 6,558,381 B2 | 5/2003 | Ingle et al. | |
| 6,572,639 B1 | 6/2003 | Ingle et al. | |
| 6,579,266 B2 | 6/2003 | Mosel et al. | |
| 6,587,731 B1 | 7/2003 | Ingle et al. | |
| 6,629,535 B2 | 10/2003 | Ingle et al. | |
| 6,685,623 B2 | 2/2004 | Presthus et al. | |
| 6,743,165 B2 | 6/2004 | Mosel et al. | |
| 6,749,624 B2 | 6/2004 | Knowlton | |
| 6,751,507 B2 | 6/2004 | Morrison et al. | |
| 6,772,013 B1 | 8/2004 | Ingle et al. | |
| 6,776,779 B1 | 8/2004 | Roy et al. | |
| 6,830,052 B2 | 12/2004 | Carter et al. | |
| 6,836,688 B2 | 12/2004 | Ingle et al. | |
| 6,840,954 B2 | 1/2005 | Dietz et al. | |
| 6,852,110 B2 | 2/2005 | Roy et al. | |
| 6,875,209 B2 | 4/2005 | Zvuloni et al. | |
| 6,879,858 B1 | 4/2005 | Adams | |
| 6,882,885 B2 | 4/2005 | Levy et al. | |
| 6,889,090 B2 | 5/2005 | Kreindel | |
| 6,976,492 B2 | 12/2005 | Ingle et al. | |
| 7,004,942 B2 | 2/2006 | Laird et al. | |
| 7,022,121 B2 | 4/2006 | Stern et al. | |
| 7,141,049 B2 | 11/2006 | Stern et al. | |
| 7,238,183 B2 | 7/2007 | Kreindel | |
| 7,294,127 B2 | 11/2007 | Leung et al. | |
| 7,998,137 B2 | 8/2011 | Elkins et al. | |
| 8,603,084 B2 | 12/2013 | Fish et al. | |
| 8,961,511 B2 * | 2/2015 | Parmer | A61B 18/1485 601/3 |
| 2002/0032441 A1 | 3/2002 | Ingle et al. | |
| 2002/0049483 A1 | 4/2002 | Knowlton | |
| 2002/0062142 A1 | 5/2002 | Knowlton | |
| 2002/0120260 A1 | 8/2002 | Morris et al. | |
| 2002/0151887 A1 | 10/2002 | Stern et al. | |
| 2002/0156471 A1 | 10/2002 | Stern et al. | |
| 2002/0183735 A1 | 12/2002 | Edwards et al. | |
| 2003/0028180 A1 | 2/2003 | Franco et al. | |
| 2003/0097162 A1 | 5/2003 | Kreindel | |
| 2003/0120326 A1 | 6/2003 | Dietz et al. | |
| 2003/0130575 A1 | 7/2003 | Desai et al. | |
| 2003/0139740 A1 | 7/2003 | Kreindel | |
| 2003/0139790 A1 | 7/2003 | Ingle et al. | |
| 2003/0144576 A1 | 7/2003 | Presthus et al. | |
| 2003/0178032 A1 | 9/2003 | Ingle et al. | |
| 2003/0195593 A1 | 10/2003 | Ingle et al. | |
| 2003/0195604 A1 | 10/2003 | Ingle et al. | |
| 2003/0199866 A1 | 10/2003 | Stern et al. | |
| 2003/0212393 A1 | 11/2003 | Knowlton et al. | |
| 2003/0216728 A1 | 11/2003 | Stern et al. | |
| 2003/0216729 A1 | 11/2003 | Marchitto et al. | |
| 2003/0220635 A1 | 11/2003 | Knowlton et al. | |
| 2003/0236487 A1 | 12/2003 | Knowlton et al. | |
| 2004/0000316 A1 | 1/2004 | Knowlton et al. | |
| 2004/0002704 A1 | 1/2004 | Knowlton et al. | |

(56) References Cited

U.S. PATENT DOCUMENTS

| | | |
|---|---|---|
| 2004/0002705 A1 | 1/2004 | Knowlton et al. |
| 2004/0030332 A1 | 2/2004 | Knowlton et al. |
| 2004/0034346 A1 | 2/2004 | Stern et al. |
| 2004/0034400 A1 | 2/2004 | Ingle et al. |
| 2004/0049251 A1 | 3/2004 | Knowlton et al. |
| 2004/0102824 A1 | 5/2004 | Sharkey et al. |
| 2004/0111087 A1 | 6/2004 | Stern et al. |
| 2004/0111136 A1 | 6/2004 | Sharkey et al. |
| 2004/0111137 A1 | 6/2004 | Shankey et al. |
| 2004/0127895 A1 | 7/2004 | Flock et al. |
| 2004/0172291 A1 | 9/2004 | Knowlton et al. |
| 2004/0186535 A1 | 9/2004 | Knowlton |
| 2004/0193238 A1 | 9/2004 | Mosher et al. |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0236177 A1 | 11/2004 | Matlock |
| 2004/0236393 A1 | 11/2004 | Ingle et al. |
| 2004/0249425 A1 | 12/2004 | Roy et al. |
| 2004/0260368 A1 | 12/2004 | Ingle et al. |
| 2004/0267336 A1 | 12/2004 | Morrison et al. |
| 2005/0154433 A1 | 7/2005 | Levy et al. |
| 2005/0171582 A1 | 8/2005 | Matlock |
| 2005/0171583 A1 | 8/2005 | Mosher et al. |
| 2005/0187599 A1 | 8/2005 | Sharkey et al. |
| 2005/0203399 A1 | 9/2005 | Vaezy et al. |
| 2005/0288544 A9 | 12/2005 | Matlock |
| 2005/0288680 A1 | 12/2005 | Ingel et al. |
| 2006/0025837 A1 | 2/2006 | Stern et al. |
| 2006/0047331 A1 | 3/2006 | Lax et al. |
| 2006/0167533 A1 | 7/2006 | Spraker et al. |
| 2007/0078502 A1 | 4/2007 | Weber et al. |
| 2007/0083247 A1 | 4/2007 | Wyeth et al. |
| 2007/0088413 A1 | 4/2007 | Weber et al. |
| 2007/0093807 A1 | 4/2007 | Baxter et al. |
| 2007/0106349 A1 | 5/2007 | Karni et al. |
| 2007/0233191 A1* | 10/2007 | Parmer ............... A61B 18/1485 607/1 |
| 2009/0163807 A1 | 6/2009 | Sliwa et al. |
| 2011/0178584 A1* | 7/2011 | Parmer ............... A61B 18/1485 607/102 |
| 2012/0016239 A1* | 1/2012 | Barthe ................. A61B 8/0858 600/439 |
| 2012/0035475 A1* | 2/2012 | Barthe ................. A61B 8/0858 600/439 |
| 2012/0035476 A1* | 2/2012 | Barthe ................. A61B 8/0858 600/439 |
| 2012/0046547 A1* | 2/2012 | Barthe ................. A61B 8/0858 600/439 |
| 2012/0053458 A1* | 3/2012 | Barthe ................. A61B 8/0858 600/439 |
| 2012/0323181 A1* | 12/2012 | Shaw ................. A61M 25/0606 604/164.12 |
| 2013/0200549 A1* | 8/2013 | Felts ................... A61M 5/3129 264/275 |
| 2013/0303904 A1* | 11/2013 | Barthe ................. A61B 8/0858 600/439 |
| 2013/0303905 A1* | 11/2013 | Barthe ................. A61B 8/0858 600/439 |

FOREIGN PATENT DOCUMENTS

| | | |
|---|---|---|
| CN | 101229078 A | 7/2008 |
| CN | 201286935 | 8/2009 |
| CN | 101820505 A | 8/2010 |
| WO | 9510981 A1 | 4/1995 |
| WO | 96/22739 | 8/1996 |
| WO | 96/34568 | 11/1996 |
| WO | 9734534 A1 | 9/1997 |
| WO | 9819613 A1 | 5/1998 |
| WO | 9908614 A1 | 2/1999 |
| WO | 9953853 A1 | 10/1999 |
| WO | 01/00269 | 1/2001 |
| WO | 0180723 A2 | 11/2001 |
| WO | 03011158 A1 | 2/2003 |
| WO | 03053355 A2 | 7/2003 |
| WO | 2006033067 A2 | 3/2006 |
| WO | 2006034357 A2 | 3/2006 |
| WO | 2006105121 A2 | 10/2006 |
| WO | 2011034986 A2 | 3/2011 |
| WO | 2011066445 A2 | 6/2011 |

OTHER PUBLICATIONS

Chinese Office Action, Mar. 25, 2015, for Chinese App'l No. 201210069908.9, filed Mar. 16, 2012.
Chinese Office Action, Mar. 24, 2015, for Chinese App'l No. 201210069906.X, filed Mar. 16, 2012.
Extended European Search Report, Mar. 24, 2015, for European App'l No. EP13760612.5, filed Mar. 15, 2013.
U.S. Office Action, Mar. 17, 2015, for U.S. Appl. No. 12/884,108, filed Sep. 16, 2010.
U.S. Office Action, Aug. 27, 2014, for U.S. Appl. No. 12/884,108, filed Sep. 16, 2010.
U.S. Advisory Action, Jun. 26, 2014, for U.S. Appl. No. 12/884,108, filed Sep. 16, 2010.
U.S. Office Action, Feb. 6, 2014, for U.S. Appl. No. 12/884,108, filed Sep. 16, 2010.
U.S. Office Action, Oct. 9, 2013, for U.S. Appl. No. 12/884,108, filed Sep. 16, 2010.
PCT International Search Report, May 9, 2011, for Intentional App'l No. PCT/US2010/049045, filed Sep. 16, 2010.
PCT Written Opinion of the International Searching Authority, May 9, 2011, for Intentional App'l No. PCT/US2010/049045, filed Sep. 16, 2010.
Chinese Search Report, Apr. 12, 2013, for Chinese App'l No. 201220099603.8, filed Mar. 16, 2012 (with English translation).
Chinese Search Report, Apr. 12, 2013, for Chinese App'l No. 201220099605.7, filed Mar. 16, 2012 (with English translation).
Chinese Search Report, Apr. 12, 2013, for Chinese App'l No. 201220099618.4, filed Mar. 16, 2012 (with English translation).
Chinese Search Report, Apr. 12, 2013, for Chinese App'l No. 201220099620.1, filed Mar. 16, 2012 (with English translation).
Chinese Search Report, Apr. 12, 2013, for Chinese App'l No. 201220099634.3, filed Mar. 16, 2012 (with English translation).
Chinese Search Report, Apr. 12, 2013, for Chinese App'l No. 201220099648.5, filed Mar. 16, 2012 (with English translation).
PCT International Search Report, Jun. 6, 2013, for Intentional App'l No. PCT/US2013/032066, filed Mar. 15, 2013.
PCT Written Opinion of the International Searching Authority, Jun. 6, 2013, for Intentional App'l No. PCT/US2013/032066, filed Mar. 15, 2013.
Chinese Office Action, Aug. 26, 2014, for Chinese App'l No. 201210069909.3, filed Mar. 16, 2012.
Chinese Office Action, Sep. 4, 2014, for Chinese App'l No. 201210069910.6, filed Mar. 16, 2012.
Chinese Office Action, Sep. 4, 2014, for Chinese App'l No. 201210069906.X, filed Mar. 16, 2012.

* cited by examiner

Cross-section A-A 5
6

Cross-section B-B

VAGINAL REMODELING DEVICE AND METHOD

RELATED APPLICATION

This application claims the priority of Chinese application 201210069906.X, filed Mar. 16, 2012. The entire contents and disclosures of this prior application are incorporated herein by reference into this application.

FIELD OF THE INVENTION

This invention relates to devices and methods for remodeling tissue of the vagina and vulva, for example, by the application of radiant energy.

BACKGROUND OF THE INVENTION

The vaginal tissue of women is stretched during vaginal child birth; at least some of the effects of the stretching are permanent and many women have long term medical consequences. Some consequences may include sexual aspects, as may follow from excessive loosening of the vagina and its opening. Such loosening typically occurs with the first vaginal delivery, and the loosening tends to increase with subsequent vaginal deliveries. The effect of looseness in this region may include decreased pressure and friction during intercourse, and as a consequence, decreased sexual pleasure for women and their conjugal partners. Some surgical options can be exercised in an attempt to alleviate these problems. However, these surgical approaches are not highly popular because of the risks associated with an invasive procedure.

Known systems and devices for treating the vagina are less than optimal, including those using radiant energy to modify the collagen. In particular, known systems are not optimized for the manipulation of the device and the cooling of the treated tissue. In addition, existing systems may not regulate the contact with the patient's tissue optimally. Finally, known systems have not proven to be simple, lightweight or intuitive to use. Described herein are systems and devices that can solve all the above-mentioned insufficiencies of known systems.

SUMMARY OF THE INVENTION

This invention provides a device and system for remodeling the female genital tissue, the device comprising a treatment tip and one or more energy delivery elements for simultaneous cooling of the vaginal epithelium and transmission of energy for heating the tissues underneath the epithelium. The device may further comprises one or more temperature sensors for measuring the temperature at or below the epithelium; one or more directional sensors mounted on the hand piece or treatment tip; and one or more depth markers to show the depth of penetration of the treatment tip into the vagina. In another embodiment, this invention provides a device having a finger holder with electrodes for remodeling the female genital tissue.

DETAILED DESCRIPTION OF THE FIGURES

Figure 3A:
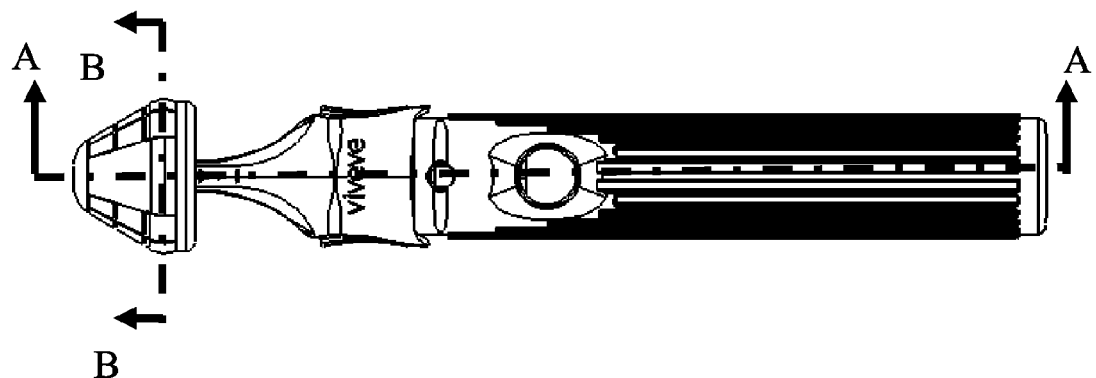
Figure 3B:
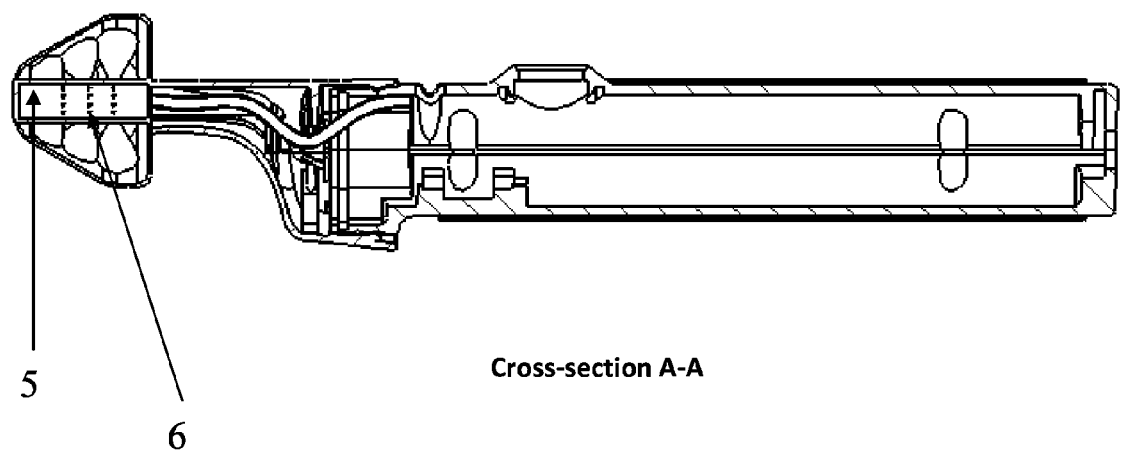
Figure 3C:
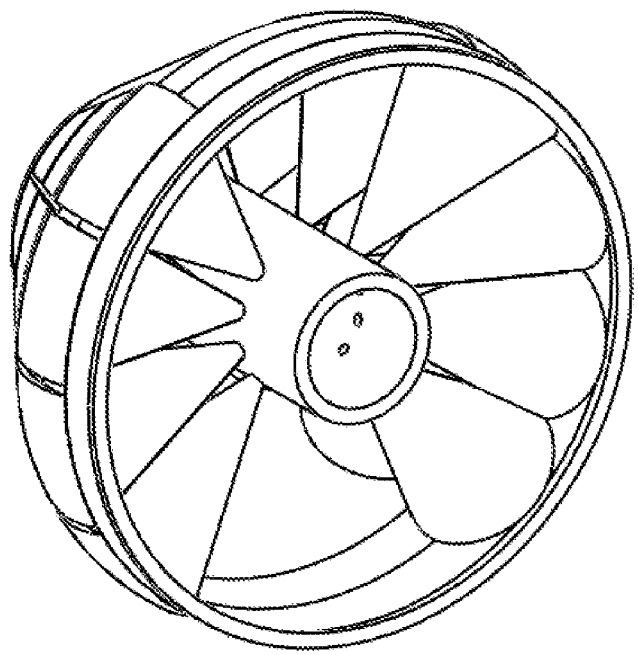
Figure 3D:
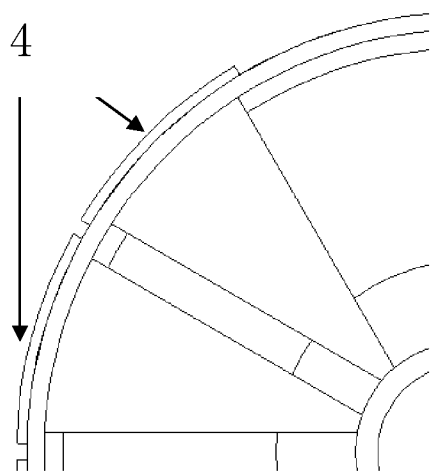

FIG. 3A indicates cross-sections A-A and B-B in an embodiment of a device comprising a cone-shaped treatment tip. FIG. 3B illustrates one embodiment of a coolant spray pattern in the internal cooling chamber (5) of a cone-shaped treatment tip, showing some of the nozzles (6). FIGS. 3C and 3D are close-up views of a coolant spray pattern, showing the energy delivery elements (4).

Figure 4:
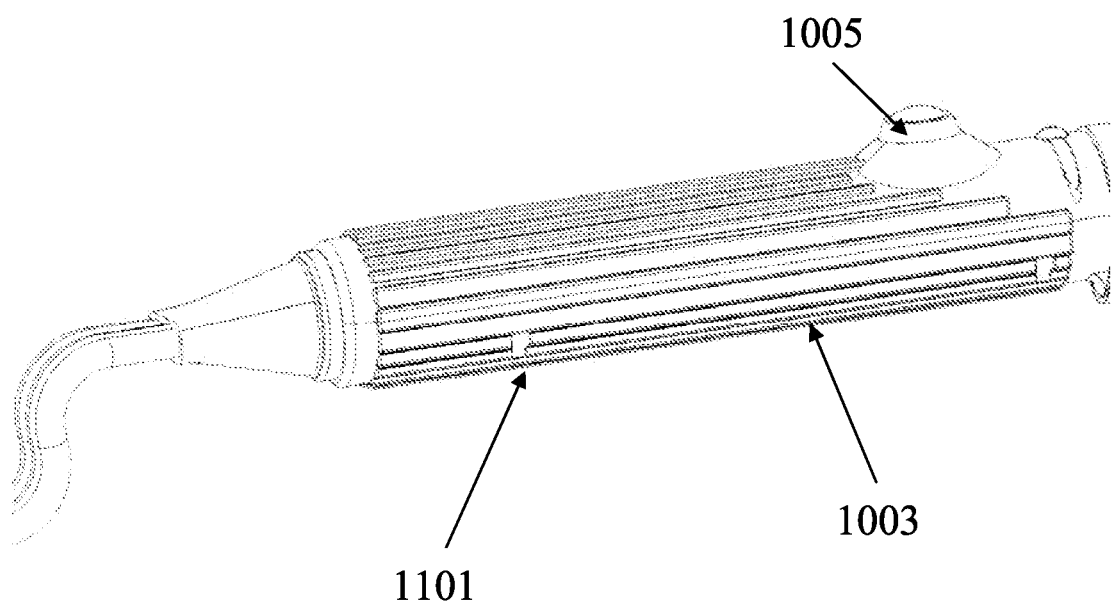

FIG. 4 illustrates one embodiment of a hand piece.

Figure 5A:
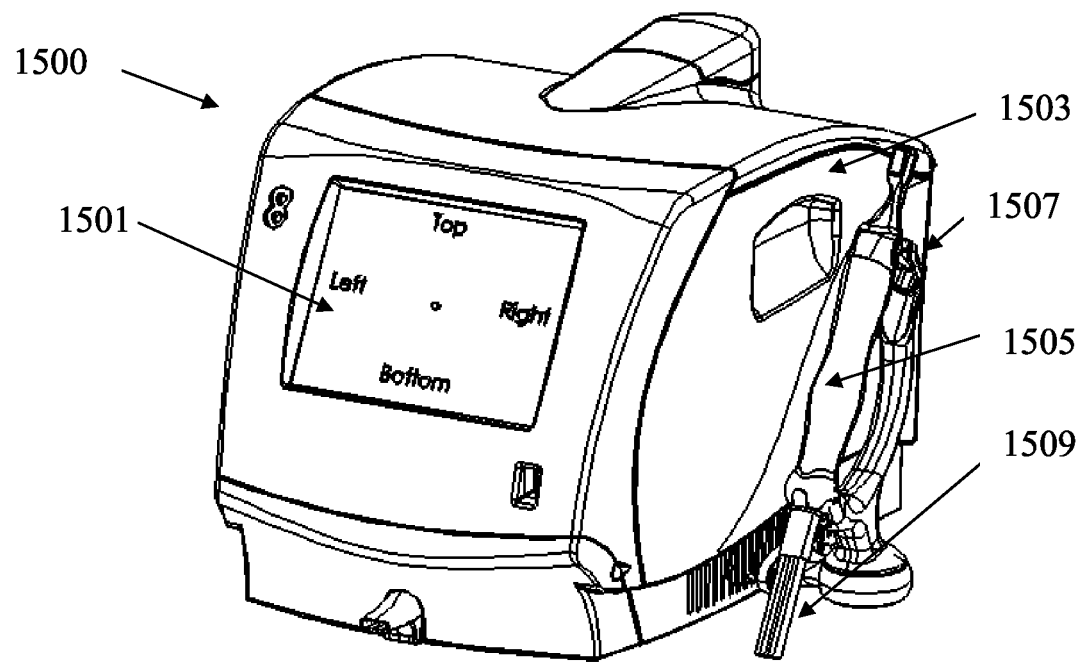
Figure 5B:
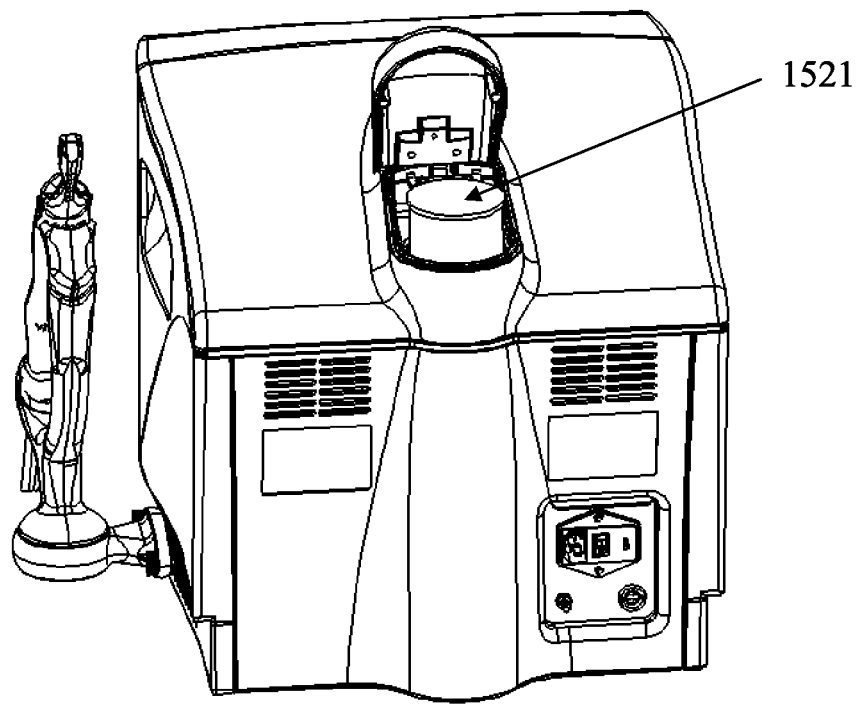

FIGS. 5A and 5B show two views of an integrated system for tissue remodeling.

Figure 6A:
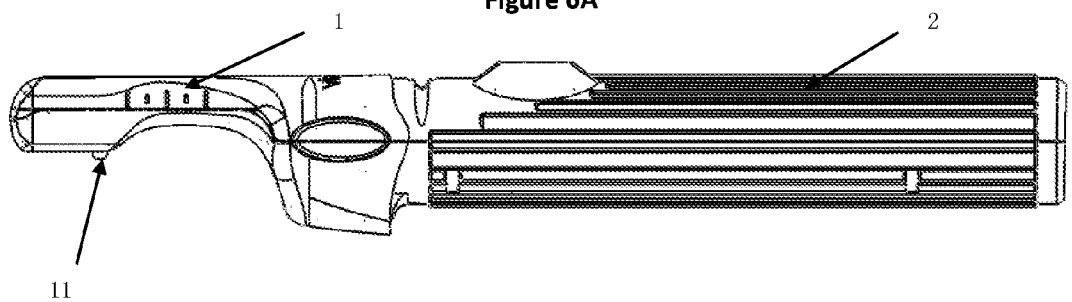
Figure 6B:
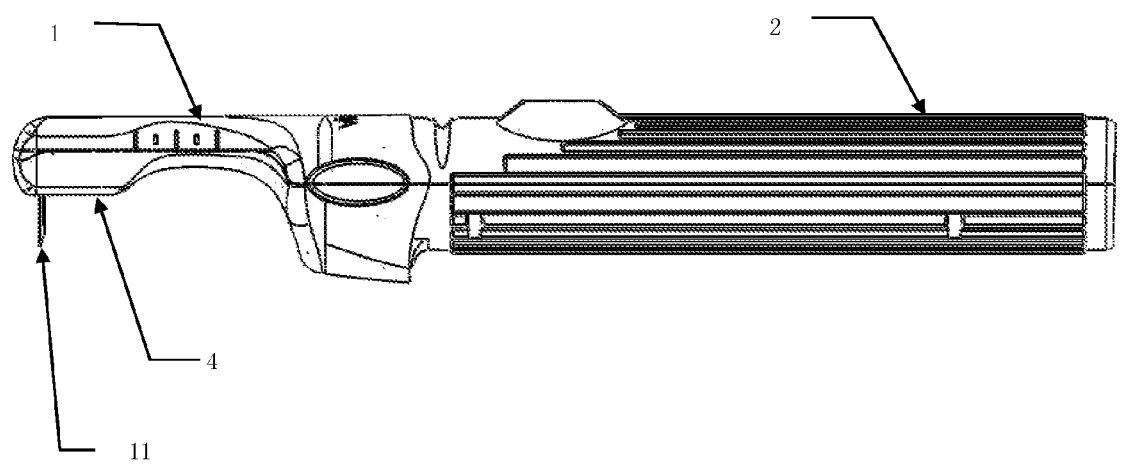
Figure 6C:
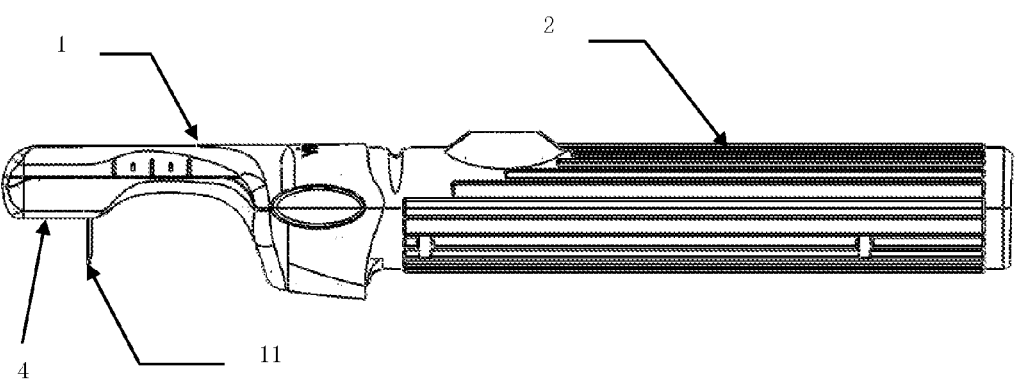

FIG. 6A shows one embodiment of a treatment device with a temperature sensor (11) that is adapted to measure temperature on the surface of the genital epithelium. FIGS. 6B and 6C show other embodiments of a treatment device with temperature sensors adapted to measure temperature beneath the surface of the genital epithelium.

Figure 7A:
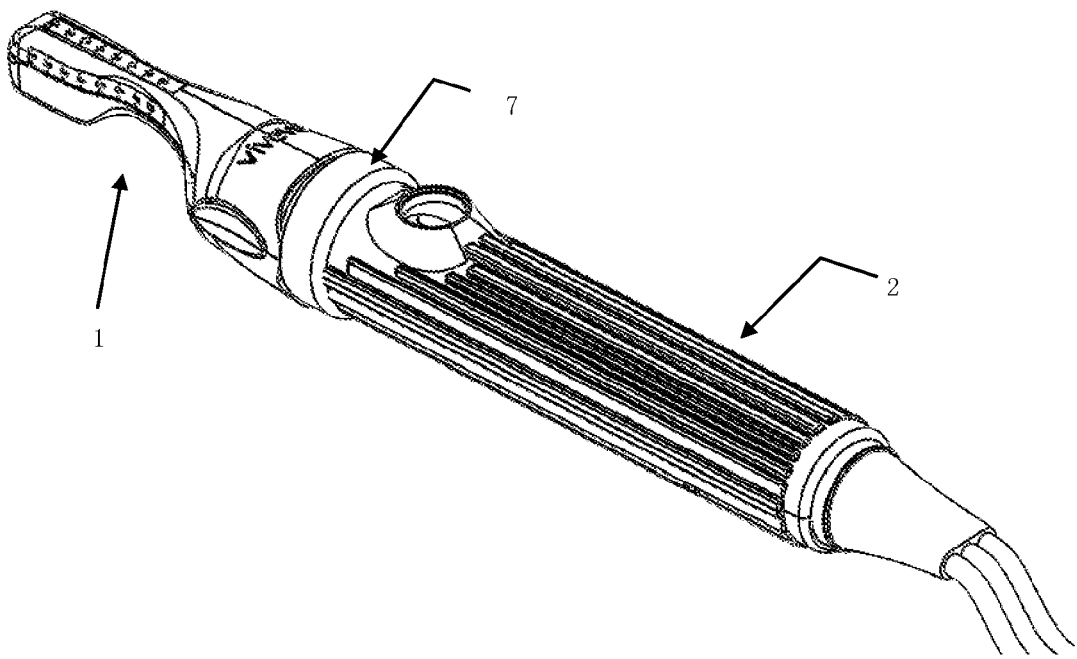
Figure 7B:
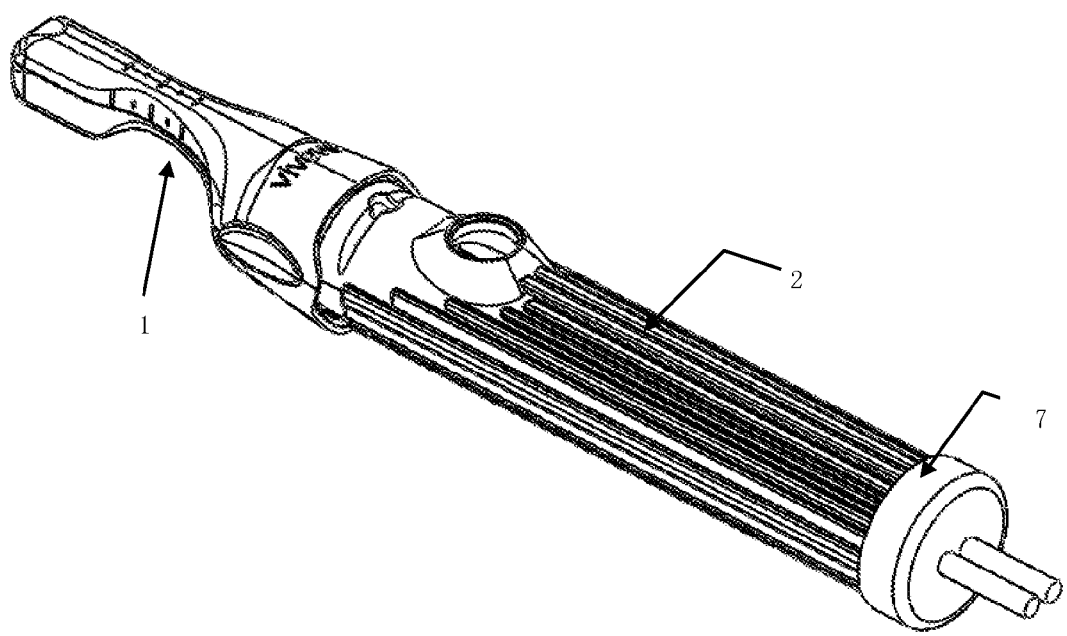
Figure 7C:
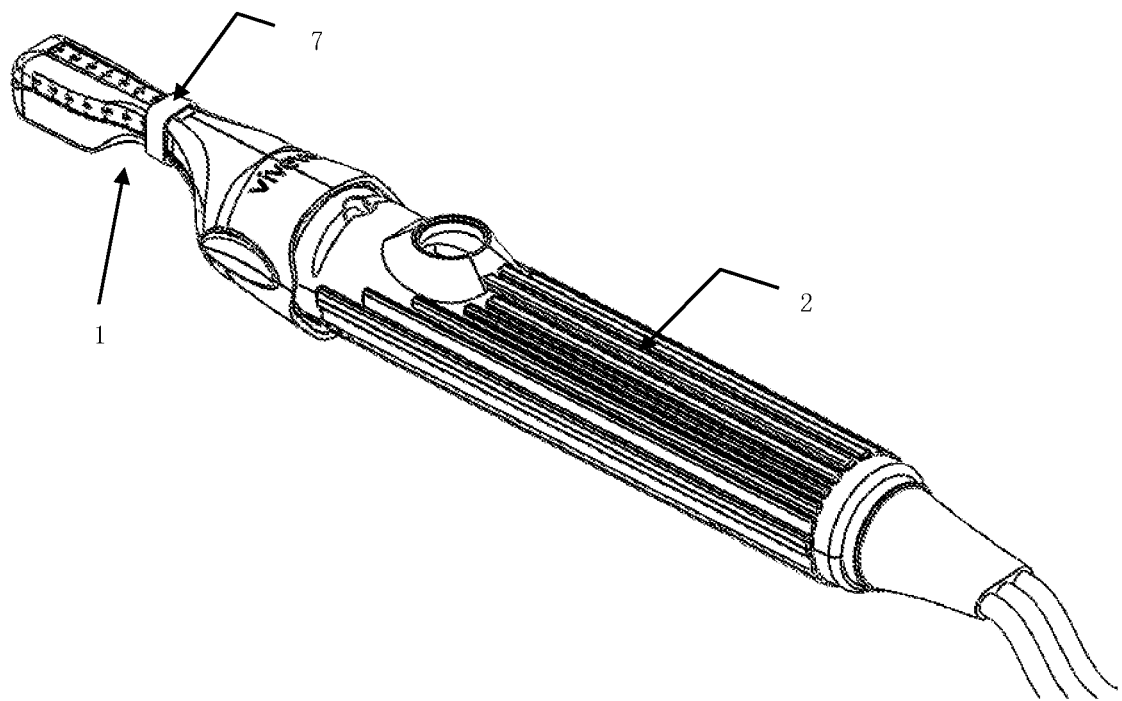

FIG. 7A shows one embodiment of a directional sensor (7) mounted on the distal end of a hand piece; FIG. 7B shows one embodiment of a directional sensor (7) mounted on the proximal end of a hand piece; FIG. 7C shows one embodiment of a directional sensor (7) mounted on the treatment tip.

Figure 8A:
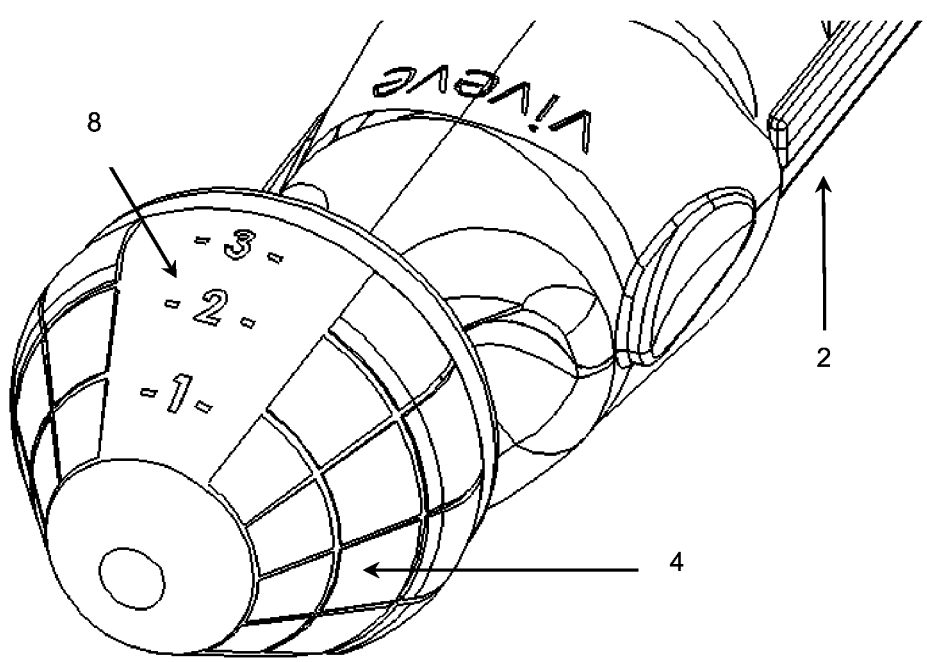
Figure 8B:
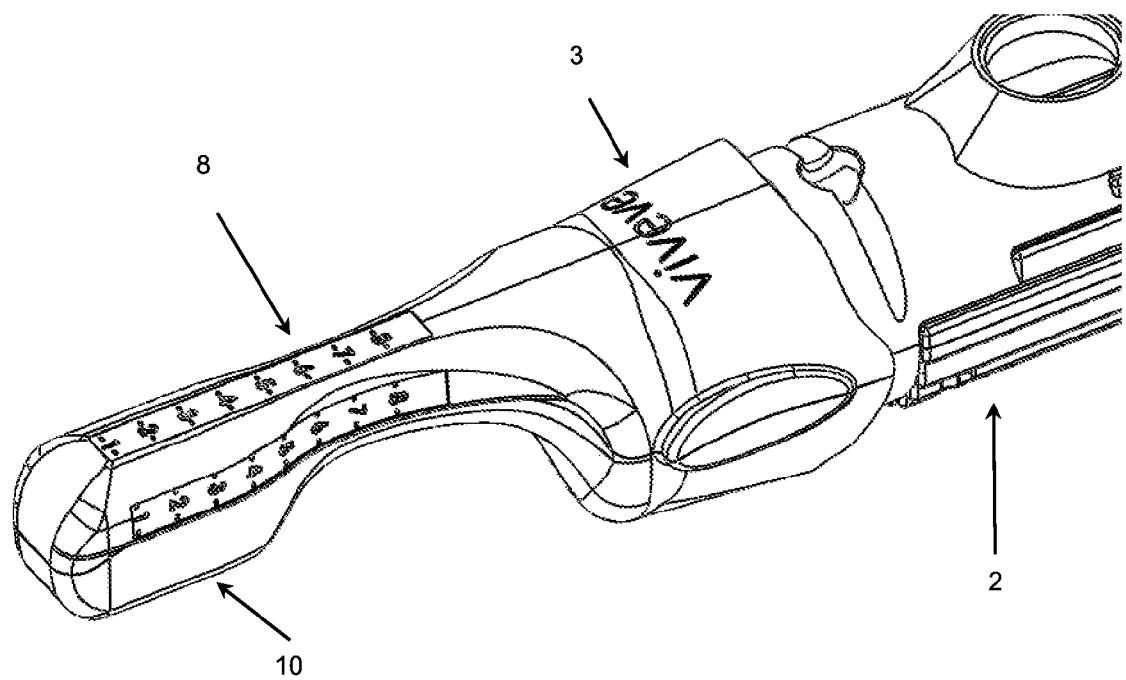
Figure 8C:
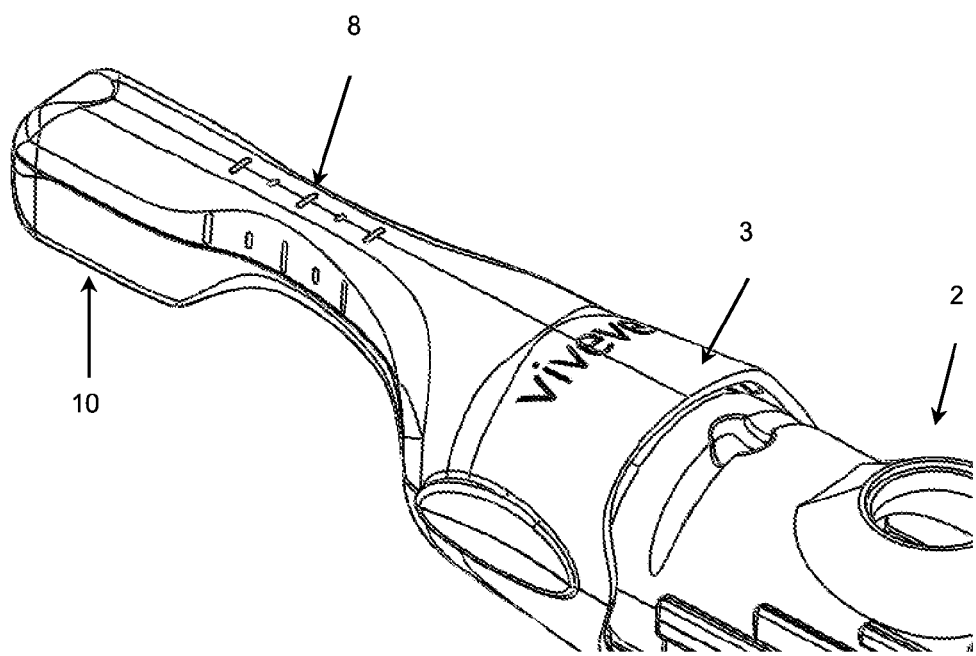

FIG. 8A shows some depth markers (8) on the treatment surface of a treatment tip having a cone-shaped distal end; FIG. 8B shows some depth markers (8) on the treatment surface of a treatment tip having a rectangular distal end; FIG. 8C shows some raised and indented depth markers on the treatment surface of a treatment tip having a rectangular distal end.

Figure 9:
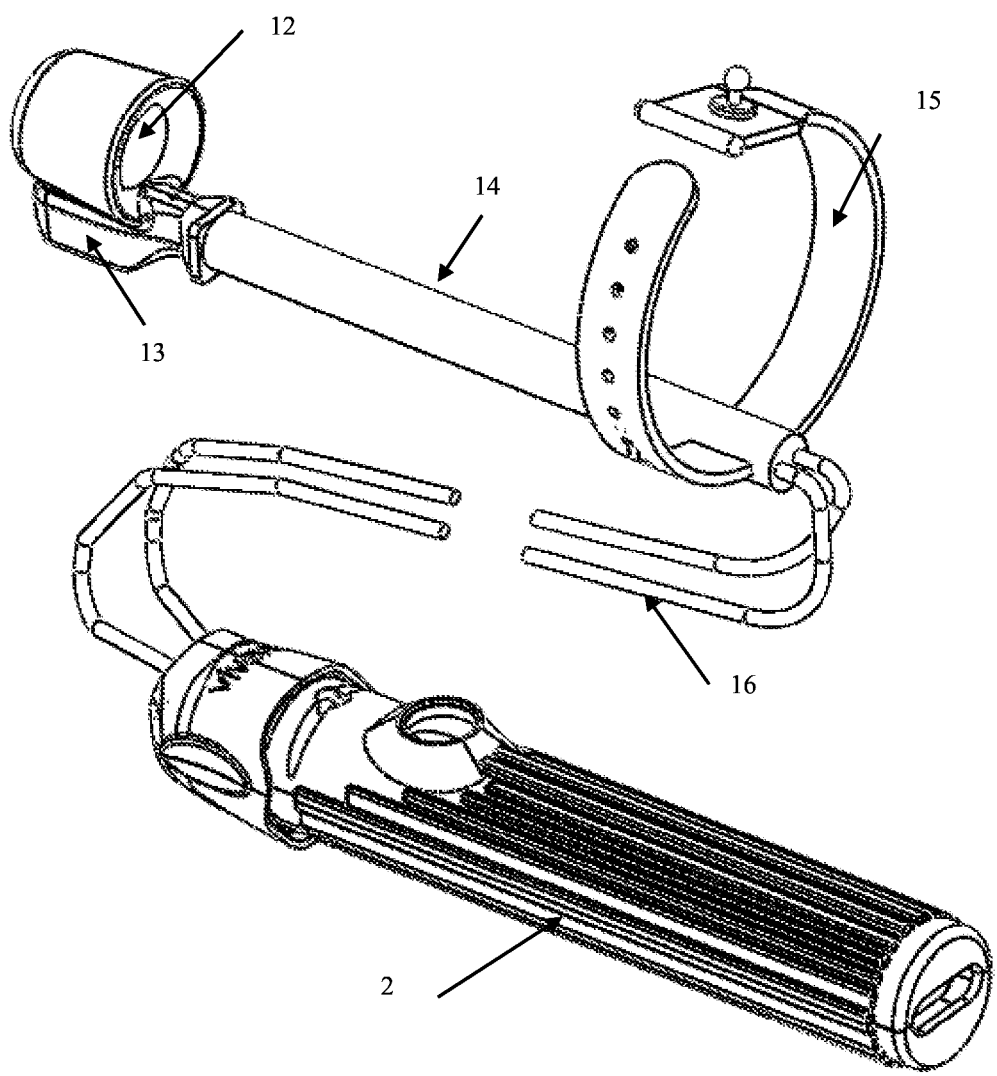

FIG. 9 shows one embodiment of a device having a finger holder with electrodes for remodeling female genital tissue, said device comprising a gripping means (14), a hand piece (2), a wrapping loop (15), a housing (13) and a wire (16).

Figure 10:
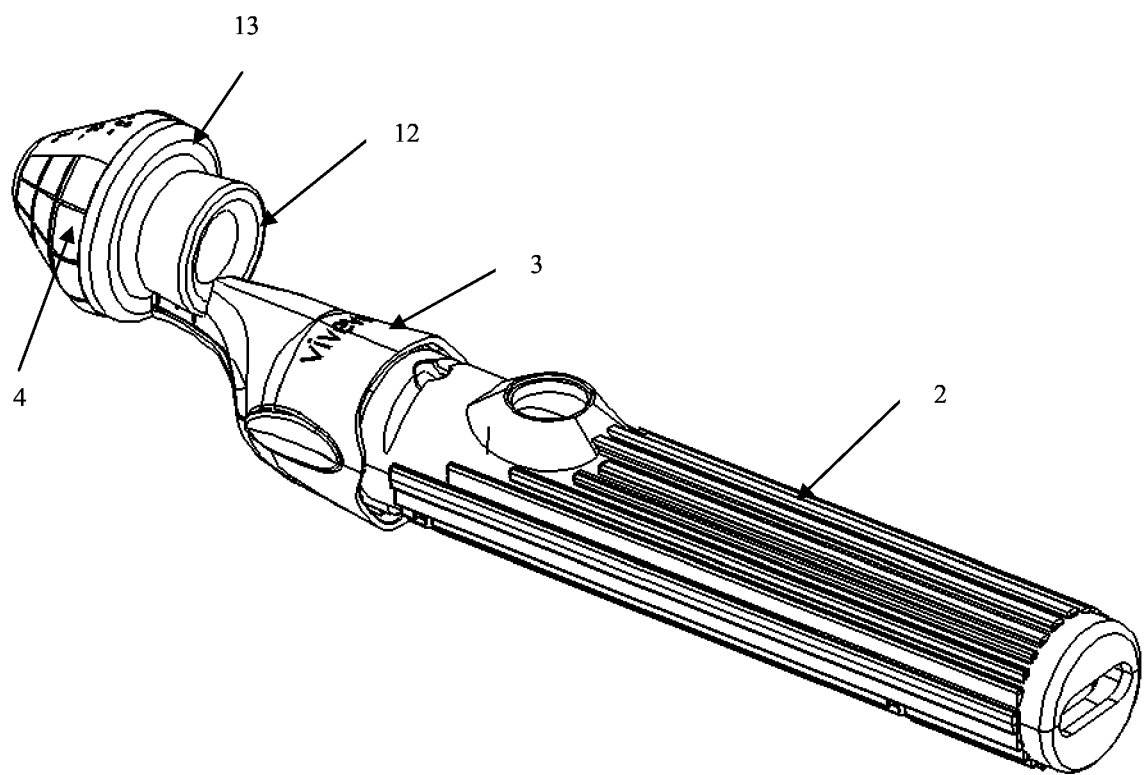

FIG. 10 shows one embodiment of a device having a finger holder for remodeling female genital tissue, wherein said finger holder (12) is coupled through a connection means (3) to a hand piece (2).

DETAILED DESCRIPTION OF THE INVENTION

Described herein are devices and systems for remodeling target tissues underlying the epithelium of female genital tissue, while cooling the epithelium. The systems consist of devices that work together as a remodeling tool. In one embodiment, the device includes a hand piece and a treatment tip, which may form part of a system further including a power source, a source of coolant, and a control system.

The present invention provides a device which is a component of systems for remodeling target tissues underlying the epithelium of female genital tissue (hereinafter called 'systems').

The device in the present invention comprises a treatment tip (1) and a hand piece (2), wherein the treatment tip (1) is coupled through a connection means (3) to the distal end of the hand piece (2), wherein the distal end of the treatment tip is conical, spherical, hemispherical, oval or circular in shape, wherein the device further comprises one or more of the following: one or more temperature sensors (11) for measuring the temperature at or below the epithelium; one or more directional sensors (7); and one or more depth markers (8) showing the depth of penetration of the treatment tip into the vagina.

In another embodiment, the device in the present invention comprises a treatment tip (1) and a hand piece (2), wherein the treatment tip is coupled through a connection means (3) to the distal end of the hand piece, wherein the device comprises one or more temperature sensors (11) for measuring the temperature at or below the epithelium, wherein the device further comprises one or more directional sensors (7) mounted on the hand piece or treatment tip. In one embodiment, the distal end of the treatment tip is rectangular, curved, conical, spherical, oval, hemispherical or circular in shape.

The distal end of the treatment tip comprises one or more energy delivery elements (4) comprising an internal surface and an epithelium-contacting surface.

The inside of the distal end of said treatment tip (1) comprises an internal cooling chamber (5) having a plurality of nozzles (6) configured to spray a coolant onto the internal surface of the energy delivery elements. Said internal cooling chamber may comprise a coolant return line that vents used coolant from the treatment tip.

The energy delivery element comprises at least one radiofrequency (RF) electrode.

The surface of the distal end of the treatment tip may be fully covered by the energy delivery elements, or has one or more areas not covered by the energy delivery elements.

In one embodiment, the energy delivery elements can be turned on and off in a specific sequence, or in a clockwise or counter-clockwise direction.

The energy delivery elements can cool the vaginal epithelium and simultaneously transmit energy for heating the target tissues.

In one embodiment, the treatment tip can be removably attached to the hand piece of a system so as to receive electricity, radiofrequency, coolant and/or digital signals.

In one embodiment, the temperature sensors are thermocouples. For example, each thermocouple comprises a first and a second junction. In one embodiment, the first junction is located on the hand piece or between the energy delivery elements and said hand piece. In another embodiment, the second junction is located at the distal end, proximal end, or middle of the energy delivery elements.

In one embodiment, the second junction comprises a blunt end that contacts the epithelium and measures its temperature, or a needle that penetrates the epithelium and measures the temperature underneath the epithelium.

Directional sensors generally provide information for tracking the position of the treatment tip. In one embodiment, directional sensors employ electromagnetic or optical mechanisms to track the position of the treatment tip. Directional sensors can be mounted on various positions such as the proximal or distal end on the hand piece or close to the energy delivery elements on the treatment tip.

In one embodiment, the surface of the treatment tip comprises depth markers, wherein the surface can be rectangular, curved, conical, spherical, hemispherical, oval or circular in shape. In one embodiment, the depth markers comprise numerical markings.

In another embodiment, the depth markers on the treatment tip or its surface comprise raised lines, indented lines or numerical markings. In another embodiment, the depth markers are located on more than one side of the treatment tip.

In another embodiment, the present invention provides a device having a finger holder fitted with electrodes for remodeling female genital tissue, said device comprising a gripping means (14) and a hand piece (2), wherein the gripping means is connected to the hand piece, wherein the gripping means has a finger holder (12) at the proximal end, and a wrapping loop (15) at the distal end, wherein the finger holder is attached to a housing (13), and the surface of the housing comprises at least one energy delivery element (4), wherein the device further comprises one or more of the following: one or more temperature sensors (11); one or more directional sensors (7); and one or more depth markers (8). In one embodiment, the finger holder and hand piece are connected via wires (16) for delivery of electricity, radiofrequency, coolant or digital signals.

In one embodiment, the present invention provides a device having a finger holder with electrodes for remodeling female genital tissue, said device comprising a finger holder (12), a hand piece (2) and a connection means (3), wherein the finger holder is coupled through the connection means to the distal end of the hand piece, wherein the finger holder is connected to a housing (13), and the surface of the housing comprises at least one energy delivery element (4), wherein the device further comprises one or more of the following: one or more temperature sensors (11); one or more said directional sensors (7); and one or more said depth markers (8).

The above-mentioned energy delivery element comprises an internal surface and an epithelium-contacting surface. In one embodiment, the energy delivery elements comprise at least one radiofrequency (RF) electrode.

The housing (13) is rectangular, curved, oval, conical, hemispherical, spherical or circular in shape. In one embodiment, the housing comprises an internal cooling chamber (5) having a supply line of coolant opposite to the internal surface of the energy delivery elements, wherein the supply line of coolant comprises a plurality of nozzles (6) configured to spray a coolant onto the internal surface of the energy delivery elements.

In another embodiment, the present invention provides a system for remodeling female genital tissue (hereinafter called 'system'). In one embodiment, the system comprises the treatment tip described above, a hand piece, and an integrated controller that comprises, for example, a housing, a radiofrequency generator within the housing, a cooling subsystem within the housing, and a controller for controlling the operation of the system.

This invention further provides a method of using the above device or system for remodeling a target tissue underlying a mucosal epithelium of the female genital tissue, comprising the step of cooling said epithelium and heating said target tissue with energy-delivery elements of the device or system. The content of PCT/US2010/049045 is hereby incorporated by reference in its entirety into this specification to illustrate a method of remodeling the female genital tissue.

The method may comprise a step of connecting the treatment tip to an elongated handle configured to be held by two hands. The method may also comprise a step of confirming contact of the energy delivery elements with the tissue based on the temperature at or near the energy delivery elements and the time since the treatment tip is last activated.

In one embodiment, the step of cooling the epithelium comprises spraying coolant onto the internal surface of the energy delivery elements, wherein the coolant may be recycled.

In said method, the target tissue may be heated to a temperature between about 45° C. and about 80° C. by applying energy from the energy delivery elements. In one embodiment, the method comprises cooling the epithelium to a temperature between about 0° C. and about 10° C. The cooling may precede the heating, and continue during the heating. Alternatively, cooling is performed during heating, and continues after heating.

In one embodiment, the method comprises contacting the epithelium with the treatment tip at one or more contact sites during a procedure.

In said method, the female genitalia include the vulva, the vagina and the introitus. The female genitalia may also include a portion of the vagina extending from the introitus inwardly from about 1 cm to about 3.5 cm. The female genitalia may include a portion of the vagina circumferentially around its wall from about 1 o'clock to about 11 o'clock, wherein the aspect closest to the urethra is at 12 o'clock. In one embodiment, the female genitalia includes a portion radiating outwardly from the introitus to the Hart's line. In another embodiment, the female genitalia includes the mucosal surfaces of the labia minora.

In said method, the target tissue includes submucosa and muscularis below the mucosal epithelium. In one embodiment, the heating does not substantially modify the mucosal epithelium of the genital tissue. In another embodiment, remodeling comprises contracting the target tissue, tightening the introitus, tightening the vagina, denaturing collagen, or tightening the collagen-rich sites in the target tissue.

This invention will be better understood by reference to the examples which follow. However, one skilled in the art will readily appreciate that the examples provided are merely for illustrative purposes and are not meant to limit the scope of the invention which is defined by the claims following thereafter.

Throughout this application, it is to be noted that the transitional term "comprising", which is synonymous with "including", "containing" or "characterized by", is inclusive or open-ended, and does not exclude additional, un-recited elements or method steps.

EXAMPLES

Device for Remodeling Genital Tissues

Figure 1:
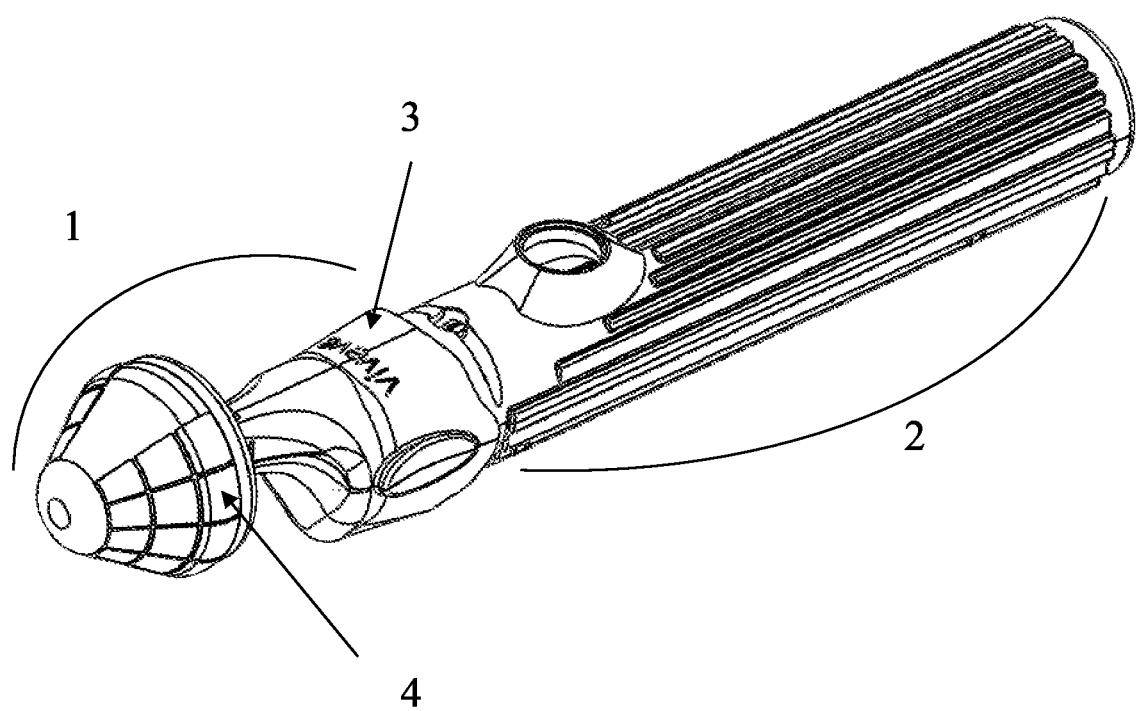
FIG. 1 is a perspective view of one embodiment of the device comprising a treatment tip (1), a hand piece (2) and a connection means (3), wherein said treatment tip has a cone-shaped distal end, wherein energy delivery elements (4) are arranged over the curved surface of the cone.
Figure 2A:
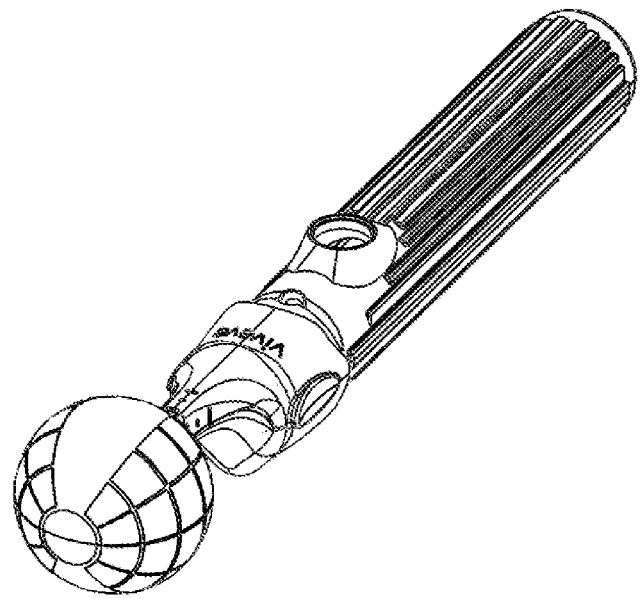
FIGS. 2A and 2B are perspective views of another embodiment of a device comprising a hand piece connected to a treatment tip that has a spherical distal end.
Figure 2B:
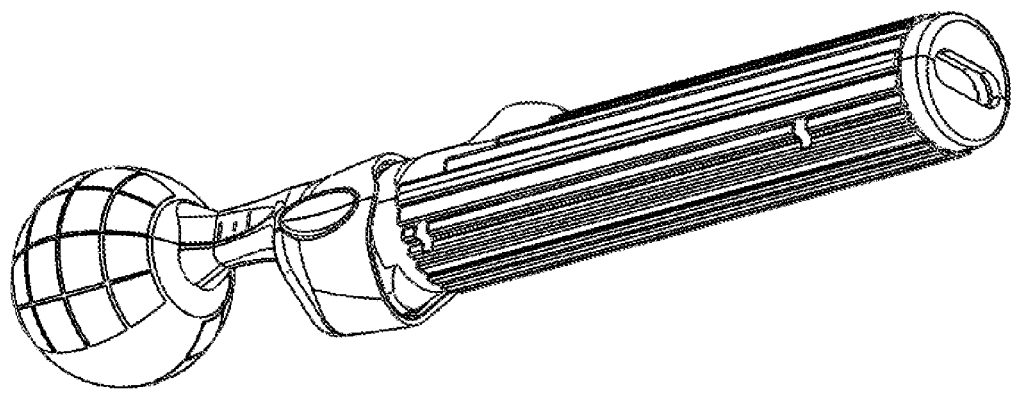

In one embodiment, a device for remodeling female genital tissue comprises a hand piece and a treatment tip (FIGS. 1-2). The hand piece is adapted to be held by an operator, such as a physician. The hand piece may include connections to a larger supporting system, or it may be operable as a self-sufficient independent device. In one embodiment, the treatment tip can be configured to be removably coupled to the hand piece, for example, the treatment tip can be designed as a quick connect/disconnect unit with respect to its attachment to the hand piece.

Treatment Tip

In one embodiment, the treatment tip comprises a housing, a midsection, and a treatment surface at the distal end of the treatment tip, wherein the treatment surface is covered by one or more energy delivery elements that each comprises an internal surface and an epithelium-contacting surface. The energy delivery elements are adapted to allow cooling of the epithelium while transmitting energy to heat the target tissue. The housing defines an interior space which extends forward to the distal end of the treatment tip. The midsection of the treatment tip provides a functional advantage in that it allows the energy delivery elements to be projected forward from the body of the hand piece. The overall length of the treatment tip can be designed to reach the innermost region of the vagina that is to be treated.

Energy Delivery Element

In one embodiment, each energy delivery element has an internal surface facing the interior space within the treatment tip, and an epithelium-contacting surface facing the exterior of the treatment tip. The internal surface may be made of a metal, e.g. copper, gold, silver, or aluminum. The epithelium-contacting surface may comprise a variety of different materials, including but not limited to, polyimides, Teflon®, silicon nitride, polysilanes, polysilazanes, Kapton and similar polymers, antenna dielectrics and other dielectric materials known in the art. Other exemplary dielectric materials include polymers such as polyester, silicon, sapphire, diamond, zirconium-toughened alumina (ZTA), alumina and the like. In another embodiment, the energy delivery element is made of a composite material, including but not limited to, gold-plated copper, copper-polyimide, silicon/silicon-nitride and the like.

In one embodiment, the energy delivery element may be a radiofrequency electrode, a microwave emitter, or an ultrasound emitter. For example, the radiofrequency electrode is a capacitive electrode that couples to the epithelium. In another embodiment, the radiofrequency electrode can be either monopolar or bipolar. In the monopolar mode, radiofrequency current flows through body tissue from a return electrode which can be in the form of a conductive pad applied to another portion of the patient's body. The distal end of the treatment tip may have a pair of monopolar electrodes, a bipolar pair, or multiple bipolar pairs.

In one embodiment, the electrode may be equipped with an integrated EEROM (Electrically Erasable Read Only Memory, also known as EEPROM) programmable memory chip at any suitable location within the treatment tip. Such a chip ma provide identifying information or other information about the operational status or configuration parameters of the radiofrequency electrode to the system, such parameters may include, by way of example, the type and size of the electrode, the number of times the energy delivery element has been fired, and the like.

Treatment Surface

In one embodiment, the distal end of the treatment tip is configured to be conical, spherical, hemispherical or of any other desirable geometry, providing a treatment surface that is suitable for the treatment site. Energy delivery elements are located on the treatment surface at the distal end of the treatment tip. For example, the energy delivery elements can be arranged on the treatment surface at the distal end of a treatment tip that may be conical, spherical, hemispherical, oval, circular or any other desirable geometry. One of ordinary skill in the art would readily design treatment surface (conical, spherical, etc.) and energy delivery elements in different sizes (e.g. small, medium and large) to accommodate anatomical differences of the female genital.

The energy delivery elements (or electrodes) can be arranged on the treatment surface in a number of different patterns or array (FIGS. 1-2). For example, the electrodes may or may not occupy the entire treatment surface. One of ordinary skill in the art would readily configure the dimensions of the energy delivery elements to suit the treatment needs and the configuration of the treatment tip so that the treatment surface and the electrodes would adequately cover the anatomy of the target tissue. By dividing the electrodes into multiple arrays and through the use of sensory technology, an operator may determine which array areas are making appropriate tissue contact and then deliver radiant energy to those specific electrodes.

In one embodiment, certain areas on the treatment surface are covered by an insulated material, not the energy delivery elements; therefore, the electrodes or energy delivery elements are absent from certain areas on the treatment surface (FIGS. 1-2). This allows the user to avoid treating certain areas of the tissue under treatment to improve the safety and effectiveness of the treatment.

In another embodiment, the electrodes are present throughout the treatment surface, but specific electrodes can be turned on/off so that treatment is avoided in certain portions of the tissue under treatment.

In yet another embodiment, the electrodes can be turned on and off in any sequence or pattern to provide treatment to the target tissue. For example, the electrodes may be turned on and off in a clockwise or counter-clockwise direction. In another embodiment, through remote control by means of a user interface, specific electrodes can be turned on and off in any sequence or pattern. In yet another embodiment, software programs can be used to track which electrodes have been turned on and turned off to identify and segregate untreated areas from treated areas.

Cooling Mechanism

In one embodiment, the interior space of the distal end of the treatment tip accommodates a cooling system to cool the energy delivery elements. For example, the interior space comprises a cooling lumen for conveying coolant to a plurality of nozzles. Various coolants are known in the art, e.g. 1,1,1,2-tetrafluoroethane (R134A) or carbon dioxide, which can be stored in a reservoir under pressure. The nozzles are typically located opposite to the internal surface of the energy delivery elements. The coolant, upon release from the nozzles, is sprayed onto the internal surface of the energy delivery elements and cools the energy delivery elements as the coolant undergoes a liquid to gas transformation. Consequently, the exterior surface (the epithelium-contacting surface) of the energy delivery elements would cool the epithelial tissues in contact with said surface.

One of ordinary skill in the art would recognize that any appropriate coolant and internal cooling system may be used. In some variations, the cooling may be electrical (e.g., via Peltier effect or the like). Thus, in general, the cooling system of the treatment device may include a cooling chamber. The cooling chamber may include one or more nozzles for spraying or applying coolant. Coolant may be applied in any appropriate pattern to the internal surface of the energy delivery elements. For example, the spraying pattern may be overlapping circles. In FIG. 3, the energy delivery elements are located on a cone-shaped treatment surface, and the nozzles are spaced opposite to the internal surface of the energy delivery elements and emit a cone-shaped spray pattern.

Thus, in general, the cooling chamber has a plurality of nozzles for applying coolant onto the internal surface of the energy delivery elements. Since the internal surface of the energy delivery elements is thermally conductive, cooling the internal surface (even a portion of the internal surface) will result in cooling the outer surface of the energy delivery elements, and thereby cooling the epithelial tissue in contact with the energy delivery elements.

Hand Piece

In general, the hand piece is sufficiently long to be easily held by two hands. The hand piece may be relatively rigid (as compared to the flexible, typically flat cable, for example). In one embodiment, the hand piece (1101) is elongated, and includes a grip region (1003) (FIG. 4). The hand piece may also include one or more controls such as a button, slider, dial, or the like. The control may allow the user to apply energy to the energy delivery elements, to apply coolant, or both. The hand piece may also include one or more indicators for indicating the status and/or orientation of the device, such as the treatment tip. For example, an indicator may indicate whether or not the treatment tip is attached; whether or not the device is out of coolant; or whether or not the device is ready for activation. In another embodiment, an indicator may indicate the temperature of the treatment tip (e.g., the energy delivery elements), and/or the duration of time that the device has been active. In some variations, the indicator includes one or more lights (e.g., LEDs, etc.), colors (including colored lights), alphanumeric display (e.g., a display screen or monitor), or the like. The hand piece is typically configured to couple with the treatment tip. In some variations, the treatment tip is configured to be capable of quickly or easily attached to and detached from the handle.

In one embodiment, either the hand piece or the treatment tip, or both, may include markers that indicate how deep into the vagina the device has entered. This may allow the user to maintain a desired depth of operation.

In one embodiment, the treatment tip is designed as a single-use disposable component, while the hand piece is typically reusable. Accordingly, the entire treatment tip and its parts are to be sterilized, and individually packaged to maintain sterilized until the package is opened, and the treatment tip is attached to a hand piece in preparation for use.

Electronic Support System for the Device

The device described above for remodeling female genital tissue may be included in a larger electronic system. The system may include a power source, such as a radiofrequency power source that provides energy to the radiofrequency electrodes. The system may also include a multiplexer driven by a controller, which can be a digital or analog controller, or a computer. When the controller is a processor (such as a microprocessor of a computer), it can include a CPU coupled through a system bus. There may also be a keyboard, disk drive, or other nonvolatile memory systems, a display, and other peripherals on the system. A program memory and a data memory may also be coupled to the bus.

In another embodiment, the electronic support system may include an operator interface comprising operator controls and a display. The operator controls can be coupled to different types of imaging systems including ultrasonic and impedance monitors. Current and voltage are used to calculate impedance. A diagnostic phase can be initially run to determine the level of treatment activity. This can be done through ultrasound as well as other means. Diagnostics can be performed both before and after treatment.

One of ordinary skill in the art would readily design an appropriate electronic support system for the device. Circuitry, software and feedback to controller result in full process control and are used to change power, the duty cycle, monopolar or bipolar energy delivery, flow rate and pressure, and can also determine when the process is completed through time, temperature and/or impedance. Furthermore, a controller can provide multiplexing, monitor circuit continuity, and determine which radiofrequency electrode is activated. When the values exceed the predetermined temperature or impedance values, a warning can be given on the display. Additionally, the delivery of radiofrequency energy to the electrodes under warning can be decreased or multiplexed to another electrode.

System for Remodeling Target Tissues

In one embodiment, a vaginal remodeling system (hereinafter called 'system') may include a hand piece, a disposable (or reusable) treatment tip, a power source or supply, a cooling sub-system, and a controller. In some variations, the controller, power supply or source and cooling sub-system may be integrated into a single unit to which the hand piece and treatment tip may be coupled (FIGS. 5A and 5B). The integrated system (1500) in this example includes a display (1501) and a housing (1503) to which the hand piece (1505) and treatment tip (1507) are attached via a cable (1509). The cable may include supply and return coolant lines, as well as a connection to the radiofrequency energy supply and any sensors on the treatment device. This entire system may be configured for ease of use, including portability and compact arrangement.

For example, in one variation, the system may include: a treatment tip (for delivery of radiofrequency energy), a source of coolant (e.g., cryogen), a hand piece, a cable connecting the hand piece and treatment tip to the source of coolant, power source, and/or control system or a controller.

In one embodiment, the hand piece is connected via a single cable to an integrated controller, which includes both a cooling system and power source that may be controlled or regulated by the controller. The cable may include supply and return coolant lines, as well as a connection to the radiofrequency energy supply and any sensor(s) on the treatment device.

In one embodiment, the integrated system may include an opening into which a coolant may be inserted. For example, the coolant may be a pressurized canister (1521) of any appropriate cryogen. The coolant canister may be threaded with one or more sets of threads to secure it into place in the integrated system, although any appropriate sealing mechanism for the coolant may be used. The level of coolant may be monitored by the system, and the display may include an icon indicating the level of coolant remaining in the canister or system.

In one embodiment, the components of the integrated controller include a microprocessor (which may include hardware, software, and/or firmware) for controlling the system, any outputs (e.g., monitor, one or more speakers, etc.), the radiofrequency power source, and the cooling sub-system. These different components of the integrated controller may be individually installed within the housing in a "modular" manner.

The overall weight and footprint of the integrated system, and particularly the integrated controller, may be sufficiently small so that the system for tissue remodeling is portable and readily storable. For example, the entire system may weigh less than 50 pounds.

The system may also include one or more controls for controlling the device. In particular, the system may include a control for controlling the energy delivery of the treatment device (e.g., activation control), as well as one or more controls for controlling the treatment regime.

The controller may include a display that is configured to display information about the procedure, the coolant, the treatment tip, handle and other components of the system. This information may be displayed on the front of the integrated controller, and may present the information with audio signals as well. The display may also be used to display error information (including error codes) based on the status of the various system component (e.g., coolant level, contact with skin, radiofrequency generator status, etc.) In one embodiment, the display screen is a touch screen that allows the user to select treatment parameters by touching the screen. In some variations, the system may include a keyboard, mouse, trackball, or the like.

In some variations, the activation control is on the hand piece, e.g. a button. In one embodiment, the system may include a wired or wireless foot switch or other control that is separate from the hand piece. In one variation, the foot switch is connected to the integrated control.

Temperature Sensors

One of the factors that need to be controlled during treatment is the temperature of the area being treated. This can be achieved through a temperature sensor such as a thermocouple. All temperature sensors known in the art can be used. A sensory device such as a thermocouple works by comparing the difference in temperature between two junctions. One of the junctions is a reference junction and the other is placed at the target area.

In one configuration of the invention, a junction of a thermocouple is placed on the treatment electrode/energy delivery elements. For example, to measure temperature on the surface of the genital tissue, a junction is designed to be a short blunt needle that is innocuous and would not cause injury to the tissue (FIG. 6A). Alternatively, to measure temperature underneath the epithelium, a junction is designed to comprise a needle that penetrates the epithelial tissue and reaches a specific depth of the target tissue where temperature data is gathered (FIGS. 6B-6C).

In one embodiment, the junction in contact with the target tissue may be positioned at the distal end or center of the energy delivery elements, or close to the proximal end of the hand piece (FIGS. 6A-6C).

In another embodiment, there may be more than one pair of temperature measuring junctions placed on the energy delivery elements in contact with the target tissue. This will allow for comparative temperature measurements or for temperature monitoring across the energy delivery elements.

In one embodiment, the reference junction of the thermocouple that is not contacting the tissue may be placed between the energy delivery elements and the hand piece, or on the hand piece.

Feedback obtained from the temperature measurement can be fed into a control unit and be displayed, and/or used for producing alarms as necessary. The temperature feedback may also be used to assess treatment effectiveness or to shut off the treatment when a target temperature has been reached or exceeded. The alarms and messages may be in the form of visual readouts and/or audio outputs.

Directional Sensors

In a typical treatment procedure, the energy delivery elements on the distal end of the treatment tip can contact various sites in the lower vagina. A set of contact sites would collectively form a treatment area on the vaginal epithelium. The energy delivery elements (or the treatment surface comprising the energy delivery elements) can be applied to the contact sites or treatment area in many ways. For example, the energy delivery elements can treat the contact sites in a clockwise or counter-clockwise manner, or at pre-determined time intervals. Since treatments may vary from patient to patient, or even within the same patient, directional sensors are integrated into the device to provide the user with appropriate information on the position of the treatment tip. In one embodiment, sensory information may be obtained from more than one sensor in the tissue remodeling system, and the sensory information from each sensor can be used individually or collectively.

A number of sensory feedback mechanisms generally known in the art can be used in the present invention. In one embodiment, the sensory feedback may be obtained through electromagnetic sensory mechanisms or through sensors like accelerometers or gyroscopes, where an initial position is noted and any changes in position are noted by changes in distance, angle or other comparative means, such as changes in yaw, pitch, or roll etc.

In another embodiment, sensory feedback can also be obtained through optical means through the measurement of light. For example, optical encoder discs are used to measure changes in position using a light source and photo or reflective sensors.

In another embodiment, sensory feedback can also be obtained through optical means through the measurement of light. For example, optical encoder discs are used to measure changes in position using a light source and photo or reflective sensors.

In one embodiment, the directional sensors may be positioned proximally or distally on the hand piece (FIGS. 7A-B). In another embodiment, the sensors can be positioned near the energy delivery elements on the treatment tip (FIG. 7C).

In one embodiment, sensory information from the directional sensors is processed and displayed to alert users as to the current position of the treatment tip, other positions it has been in, the direction of treatment and other pertinent information.

In another embodiment, sensory information obtained from a treatment device may activate alarms indicating if the treatment device is approaching a new treatment site, if it is traversing a site that has already been treated, there has been a change in the treatment direction.

Sensory information regarding the treatment process for a given patient may be stored as reference and used for comparison in future treatments or other purposes.

Sensory information obtained from the directional sensors would have many applications. For example, it provides information on the specific location of the treatment device on the treatment area. In treating patients, it may be necessary to vary the energy delivery scheme, the quantity of energy delivered, coolants or other components used to assist treatment, etc. Thus, the position of the treatment device on the treatment area can be used for one or more purposes:

1. The position of the treatment device may indicate whether or not treatment or any supplementary components would be necessary. Thus, information regarding the position can be used to determine whether the treatment should be started or stopped, and if use of any supplementary materials (e.g. coolants) need to be started or stopped.
2. The position of the treatment device may be used to vary the amount of energy delivered, or the amount of any supplementary materials used. These changes may improve the efficiency and safety of the treatment. Thus, based on the changes in the position of the device, and the direction of movement of the device towards specific treatment areas, various treatment parameters may be changed.
3. The changes in the treatment materials and/or parameters can either be programmed directly into the treatment control device, or be manually controlled if necessary.

Depth Markers

In one embodiment, the tissue remodeling device described above can be used to treat vagina of different shapes and depths. The depth at which the treatment surface at the distal end of the treatment tip penetrates the vagina or other target tissue can affect the safety and/or effectiveness of the treatment. Accordingly, markers on the treatment device allow a user to quickly assess the depth at which the treatment surface/treatment device has penetrated the vagina. The location of the markers will depend on the configuration of the device itself.

In one embodiment, scale markers accompanied by raised reference lines or other similar features help the user either visually or through sense of touch to determine the depth of penetration. Alternatively, the scale markers are indented instead of raised. In another embodiment, the scale markers can be raised markers on one side of the treatment tip and be indented markers on another side. Any of the above marker schemes can be placed on one or more sides of the treatment tip to help the user manipulate the device while maintaining it at a specific depth within the vagina.

In case the distal end of the treatment tip is conical (or spherical, circular, etc.) in shape, depth markers (8) can surround the treatment surface or cover part of the surface (FIG. 8A). This will be useful when the treatment device is rotated or inserted during the treatment process.

In one embodiment, numerals can be used as depth markers to show the depth of penetration (FIGS. 8A, 8B). This numeric scale can include numbers and unit of measurement such as inches, millimeters or centimeters. These numbers can be printed on the treatment tip, flush with the surface of the treatment tip. In another configuration, the numbers may be raised or indented to enhance the visual effect and sense of touch.

The numeric markers may also be printed with colors that substantially contrast the color of the treatment tip. For example, if the treatment tip is black, the markers could be white, or vice versa. This color contrast will allow for easy visual recognition of the treatment depth.

In another embodiment, the numbers and markers can be staggered in multiple colors to display different depths of penetration, such as using three different colors to depict shallow, medium or deep.

In another embodiment, the numbers and markers can be staggered with two different colors as safety indicators. A certain depth may be considered safe, and this may be indicated using green color for example, and a depth considered unsafe may be indicated using red. Other contrasting colors could also be used.

In summary, markers located on the treatment tip enable the user to quickly determine if the tissue remodeling treatment tip has reached the depth of the target vaginal tissue. The markers and numerals are located on the treatment surface at the distal end of the treatment tip. In another embodiment, the markers are near the proximal end of the treatment tip. In yet another embodiment, the markers could be located at multiple positions on the treatment tip for added convenience.

Device with Finger Holder

In one embodiment, the treatment device comprises a gripping means (14) and a hand piece (2), wherein the gripping means is connected to the hand piece, wherein the gripping means has a finger holder (12) at the proximal end, and a wrapping loop (15) at the distal end, wherein the finger holder is connected to a housing (13), and the surface of the housing comprises at least one energy delivery element (4) (FIG. 9).

In one embodiment, the finger holder is connected to a rod and a strap that can wrap around the user's hand or arm so that the device may be held firmly (e.g. a wrist band, see FIG. 9). This will allow the user to access and withdraw from the treatment site without losing the grip, thus promoting safety, treatment effectiveness and user comfort.

In one embodiment, the finger holder (12) is connected to the hand piece (2) via wires (16) to deliver electricity, radiofrequency, coolant and/or digital signals. The housing (13) is rectangular, curved, oval, conical, hemispherical, spherical or circular in shape.

In another embodiment, the finger holder is connected to the hand piece without the rod and wristband (FIG. 10). This will allow a user to pull his/her finger out of the finger holder and just grasp the hand piece after the energy delivery elements have been placed into the treatment site. The treatment device comprises a finger holder (12), a hand piece (2) and a connection means (3), wherein the finger holder is coupled through the connection means to the distal end of the hand piece, wherein the finger holder is connected to a housing (13), and the surface of the housing comprises at least one energy delivery element.

In one embodiment, the finger holder can be designed to accommodate a wide variety of finger sizes, both male and female. One way to achieve this would be through the use of finger holders and electrodes of matching sizes, or the use of sleeves of different internal diameters inside the finger holder. Another approach is making the finger holder with soft materials that will adapt to various finger sizes. The finger holder will allow the physician/user/treatment provider to easily reach the treatment site, thus achieving different advantages such as accuracy and speed of treatment.

In one embodiment, the energy delivery elements are part of a housing that accommodates a cooling chamber to cool the energy delivery elements. For example, the cooling chamber may comprise a cooling lumen for conveying coolant to one or more nozzles. Various coolants are known in the art, e.g. 1,1,1,2-tetrafluoroethane (R 134A) or carbon dioxide which can be stored under high pressure. The energy delivery elements comprise an epithelium-contacting surface and an internal surface facing the cooling chamber. In one embodiment, the nozzles are located opposite to the internal surface of the energy delivery elements. The coolant, upon release from the nozzles, is sprayed onto the internal surface of the energy delivery elements and cools the surface as a result of vaporization. Consequently, the exterior epithelium-contacting surface of the energy delivery elements would cool the epithelial surface of the target tissue.

Treatment of target tissue is achieved by inserting a finger into the finger holder and directly applying the energy delivery elements onto the treatment site. The energy delivery elements can be moved in a clockwise or counter-clockwise direction on the treatment site. One of ordinary skill in the art would readily configure the dimensions and sizes of the energy delivery elements to provide optimal treatment.

In one embodiment, the energy delivery element may be a radiofrequency electrode, a microwave emitter, or an ultrasound emitter. In one embodiment, the radiofrequency electrode is a capacitive electrode in contact with the mucosal epithelium.

What is claimed is:

1. A device for remodeling the female genital tissue, comprising a treatment tip and a hand piece, wherein the treatment tip is equipped with a finger holder and is connected to the distal end of the hand piece via a connection, wherein the distal end of the treatment tip is rectangular, conical, spherical, hemispherical, oval or circular in shape, and has a surface comprising one or more energy delivery elements, wherein said elements have an internal surface and an epithelium-contacting surface, wherein said treatment tip is connected to said connection via a gripping means, wherein the distal end of said gripping means is attached to said treatment tip, and the proximal end of said gripping means is connected to said connection, wherein a strap is attached close to the proximal end of said gripping means, and wherein the device further comprises one or more of the following:
   (a) one or more temperature sensors for measuring the temperature at or below the epithelium;
   (b) one or more directional sensors; and
   (c) one or more depth markers showing the depth of penetration of the treatment tip into the vagina.

2. The device of claim 1, wherein the inside of said treatment tip comprises an internal cooling chamber having a supply line of coolant opposite to the internal surface of said one or more energy delivery elements, wherein the supply line of coolant comprises a plurality of nozzles configured to spray a coolant onto the internal surface of said one or more energy delivery elements.

3. The device of claim 1, wherein the surface at the distal end of the treatment tip is fully or partially covered by energy delivery elements.

4. The device of claim 1, wherein the temperature sensors are thermocouples, each comprising a first and a second junction.

5. The device of claim 4, wherein the second junction comprises a blunt end that contacts the epithelium and measures its temperature.

6. The device of claim 4, wherein the second junction comprises a needle that penetrates the epithelium and measures the temperature below the epithelium.

7. The device of claim 1, wherein the directional sensors employ electromagnetic or optical mechanisms to track the position of the treatment tip.

8. The device of claim 1, wherein the depth markers comprise raised lines, indented lines or numerical markers.

9. A method of using the device of claim 1 for remodeling a target tissue underlying a mucosal epithelium of the female genital tissue, comprising the step of cooling said epithelium and heating said target tissue with said energy delivery elements.

10. The method of claim 9, wherein remodeling includes contracting the target tissue, tightening the introitus, tightening the vagina, denaturing collagen, or tightening collagen-rich sites of the target tissue.

11. A device for remodeling the female genital tissue, comprising a treatment tip and a hand piece, wherein the treatment tip is equipped with a finger holder and is connected to the distal end of the hand piece via a connection, wherein the distal end of the treatment tip is rectangular, conical, spherical, hemispherical, oval or circular in shape, and has a surface comprising one or more energy delivery elements, wherein said elements have an internal surface and an epithelium-contacting surface, wherein said treatment tip is connected to said connection via a gripping means, wherein the distal end of said gripping means is attached to said treatment tip, and the proximal end of said gripping means is connected to said connection, wherein a strap is attached close to the proximal end of said gripping means, wherein the proximal end of said gripping means is connected to said connection via wires, and wherein the device further comprises one or more of the following:
   (a) one or more temperature sensors for measuring the temperature at or below the epithelium;
   (b) one or more directional sensors; and
   (c) one or more depth markers showing the depth of penetration of the treatment tip into the vagina.

12. The device of claim 11, wherein the inside of said treatment tip comprises an internal cooling chamber having a supply line of coolant opposite to the internal surface of said one or more energy delivery elements, wherein the supply line of coolant comprises a plurality of nozzles configured to spray a coolant onto the internal surface of said one or more energy delivery elements.

13. The device of claim 11, wherein the surface at the distal end of the treatment tip is fully or partially covered by energy delivery elements.

14. The device of claim 11, wherein the temperature sensors are thermocouples, each comprising a first and a second junction.

15. The device of claim 14, wherein the second junction comprises a blunt end that contacts the epithelium and measures its temperature.

16. The device of claim 14, wherein the second junction comprises a needle that penetrates the epithelium and measures the temperature below the epithelium.

17. The device of claim 11, wherein the directional sensors employ electromagnetic or optical mechanisms to track the position of the treatment tip.

18. The device of claim 11, wherein the depth markers comprise raised lines, indented lines or numerical markers.

19. A method of using the device of claim 11 for remodeling a target tissue underlying a mucosal epithelium of the female genital tissue, comprising the step of cooling said epithelium and heating said target tissue with said energy delivery elements.

20. The method of claim 19, wherein remodeling includes contracting the target tissue, tightening the introitus, tightening the vagina, denaturing collagen, or tightening collagen-rich sites of the target tissue.

* * * * *